United States Patent
Göring et al.

(10) Patent No.: US 7,534,922 B2
(45) Date of Patent: May 19, 2009

(54) PROCESSES FOR THE MANUFACTURE OF ACETALS

(75) Inventors: Matthias Göring, Hofheim (DE);
Michael Hoffmockel, Niedernhausen (DE); Jürgen Lingnau, Mainz (DE); Karl-Friedrich Mück, Wiesbaden (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 11/302,290

(22) Filed: Dec. 13, 2005

(65) Prior Publication Data

US 2006/0129000 A1     Jun. 15, 2006

Related U.S. Application Data

(60) Provisional application No. 60/636,010, filed on Dec. 13, 2004.

(51) Int. Cl.
*C07C 41/56* (2006.01)
*B01J 8/02* (2006.01)

(52) U.S. Cl. .................. 568/594; 422/129; 422/211

(58) Field of Classification Search .................. None
See application file for complete search history.

(56) References Cited

U.S. PATENT DOCUMENTS

| 4,579,979 A | * | 4/1986 | Andrade et al. ............ 568/596 |
| 6,015,875 A | | 1/2000 | Smith, Jr. et al. |
| 6,379,507 B1 | | 4/2002 | Satoh et al. |

FOREIGN PATENT DOCUMENTS

| CH | 688041 | 4/1997 |
| DE | 1002305 | 2/1957 |

* cited by examiner

*Primary Examiner*—Rosalynd Keys
(74) *Attorney, Agent, or Firm*—Connolly Bove Lodge & Hutz, LLP

(57) ABSTRACT

A process for preparing acetals from aldehydes and alcohols is carried out by generating a reaction/distillation zone charged with an acidic fixed bed catalyst in a distillation column, feeding the aldehyde and the alcohol to the reaction/distillation zone and at least partly converting them to the acetal, heating the column bottom disposed below the reaction/distillation zone in order to at least partly evaporate the bottom's mixture and to establish a defined temperature in the reaction/distillation zone, feeding an extractant into a rectifying section of the column, disposed above the reaction/distillation zone and condensing a product having more than 90% by weight of acetal at the top of the column.

21 Claims, 1 Drawing Sheet

PROCESSES FOR THE MANUFACTURE OF ACETALS

This application claims benefit to Ser. No. 60/636,010, filed Dec. 13, 2004, under 35 U.S.C. 119(e).

BACKGROUND OF THE INVENTION

1. Brief Description of the Invention

The invention relates to an improved process for preparing acetals, especially water- and alcohol-free acetals. Acetals are solvents and intermediates in the chemical industry.

2. Related Art

Acetals can be prepared by acid-catalyzed reaction of alcohols with aldehydes. One industrially important acetal is methylal (formaldehyde dimethyl acetal). It is prepared industrially by acid-catalyzed reaction of aqueous formaldehyde with methanol. It is possible to remove methylal from the reaction mixture by distillation, but it is accompanied by water and methanol because the two components each form a binary azeotrope with methylal. For the solution of this separation problem, numerous processes have been proposed; most of them utilize extraction or extractive rectification in order to overcome the azeotropes.

DE 1 002 305 discloses a process for extractive distillation of water- and methanol-containing methylal with water in order to obtain methanol-free methylal.

CH 688 041 describes a process for preparing methylal from formaldehyde and methanol by reactive distillation. The reaction takes place in a distillation column with catalysis by an acidic ionic exchange resin which has been introduced into one or more column sections in suitable form. At the top of the column, the azeotrope of methylal and methanol is obtained and is worked up in the further three separating steps extraction with aqueous alkali, rectification to give the azeotrope with 0.9-1% water, final drying to remove water with an inorganic desiccant such as calcium chloride, zeolites or silica gel, to obtain approx. 99.99% pure methylal. The process has the disadvantage that, for the alkaline extraction and for the final drying, assistants have to be introduced and have to be disposed of or worked up. The reactive distillation which is advantageous in itself is followed by three further separation steps before the pure product.

U.S. Pat. No. 6,379,507 discloses a process for preparing methylal from formaldehyde and methanol, according to which the particular mixture of water, formaldehyde, methanol and methylal is withdrawn at at least four positions in a distillation column and the mixtures are each fed in forced flow to the corresponding at least four fixed bed reactors. The fixed bed reactors charged with an acidic ion exchange resin are dedicated vessels separate from the column. The apparatus demands for a plurality of separate reactors with dedicated pump and control system are considerable. The process attains a concentration of 0.3-0.4% methanol and 1.2% water at the top of the column, but only with use of a defoamer which is fed to the top of the column.

U.S. Pat. No. 6,015,875 describes a process for preparing acetals from formaldehyde and methanol by reactive distillation at elevated temperature and pressure approx. 7 bar, the acidic catalysts used being zeolites. However, the process achieves only 73-77% methylal at the top of the reactive column.

SUMMARY OF THE INVENTION

It is therefore an object of the invention to find an improved process for the preparation of acetals which requires a minimum number of separation steps, entails a minimum level of apparatus complexity, does not involve disproportionate additional complexity as a result of the introduction of aqueous alkalis as an extractant or oily defoamer, even in the first step affords a maximum product concentration of the acetal.

It has been found that, surprisingly, acetals are formed in high product concentration and yield when the reactive distillation and the extractive distillation are combined in one column, This process affords good results even when the extractant used is a reaction product, for example water, which is expected by those skilled in the art to accelerate the reverse reaction and thus to impair the yield.

Figure 1:
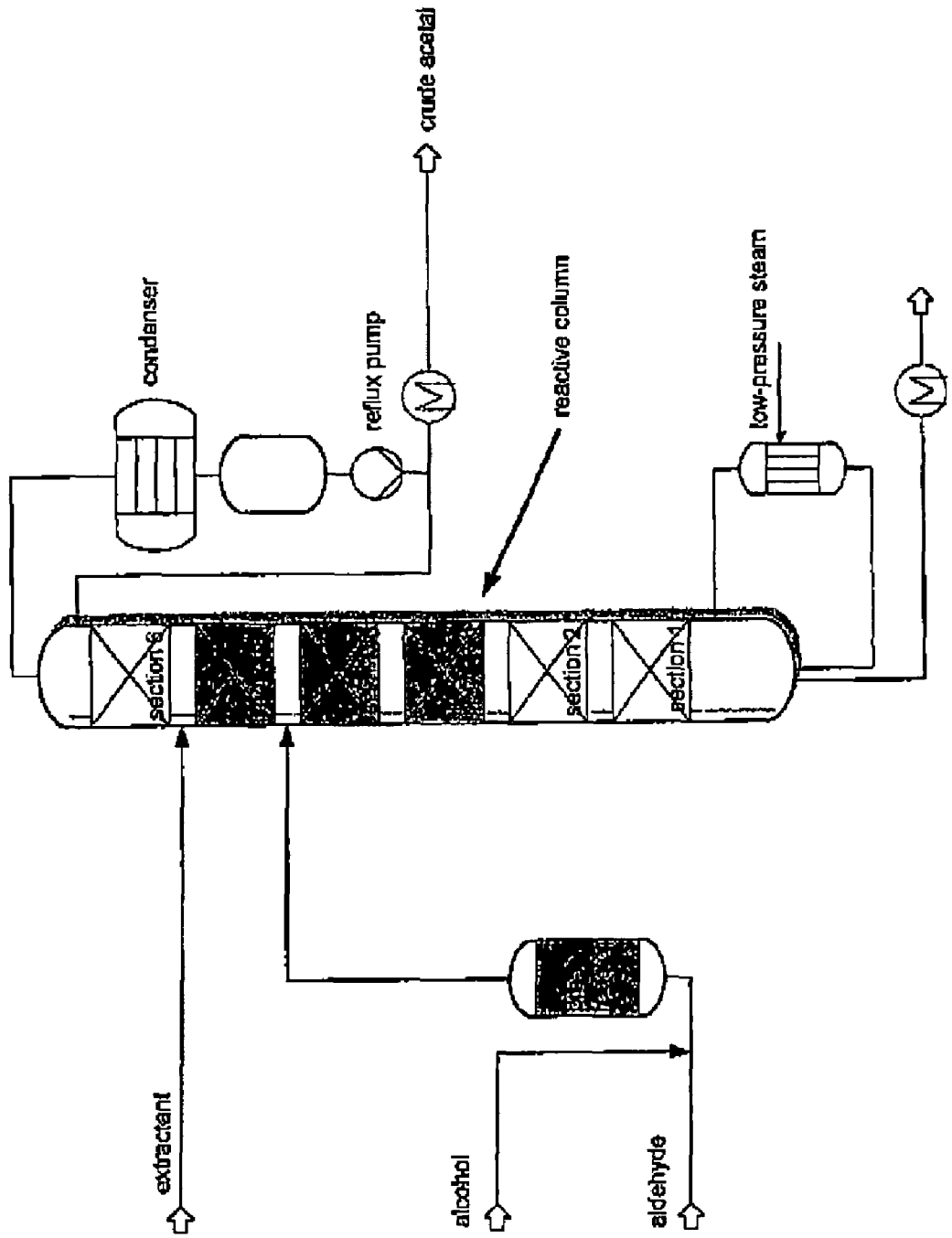
FIG. 1 illustrates an embodiment according to the invention.

The invention therefore provides a process for preparing acetals from aldehydes and alcohols by reactive distillation in one column, which comprises a) feeding aldehyde and alcohol to the reaction/distillation zone and at least partly converting them to the acetal, b) heating the column bottom disposed below the reaction/distillation zone in order to at least partly evaporate the bottom's mixture and to establish a defined temperature in the reaction/distillation zone, c) feeding an extractant into a rectifying section of the column, disposed above the reaction/distillation zone and d) condensing a product having more than 90% by weight of acetal at the top of the column.

In a preferred embodiment of the process, the reaction/distillation zone is obtained by charging one or more sections of the column with an acidic fixed bed catalyst.

In a further preferred embodiment of the process, a reflux ratio between R=0.5 and R=10 is set in the column.

In a further preferred embodiment of the process, the top product obtained in step d) of the process is concentrated to a content of at least 99% by weight of acetal in not more than two subsequent separating operations.

For the performance of the process according to the invention, suitable distillation columns are in principle those without particular apparatus requirements and which have been charged with an acidic fixed bed catalyst in one or more of their sections. Suitable acidic catalysts are acidic ion exchange resins, zeolites or else support-bound heteropolyacids. Preference is given to acidic ion exchange resins.

The process according to the invention is suitable for the preparation of any acetals by reacting suitable alcohols and aldehydes, preferably of primary aliphatic alcohols having from one to six carbon atoms with aliphatic or aromatic aldehydes. The starting materials preferably have one or two carbon atoms, specifically methanol and ethanol, and also formaldehyde and acetaldehyde. Particular preference is given to the preparation of methylal from formaldehyde and methanol. The process will be illustrated hereinbelow with reference to this preferred example.

Formaldehyde is fed to the reaction in the form of an aqueous solution. The concentration of the solution is in the range from 5 to 75% by weight, preferably from 15 to 55% by weight and more preferably from 18 to 40% by weight. For stabilization, the formaldehyde solution may already contain methanol in concentrations of from 1 to 20% by weight. This amount of methanol is taken into account in the calculation of the stoichiometric ratios. The formaldehyde solution is preferably free of metal cations because the presence of metal cations can lead to accelerated deactivation of the catalyst.

In a preferred embodiment of the invention, the reactants are not fed directly to the reaction/distillation zone in the column, but are instead first mixed and passed through a prereactor. The prereactor has been charged with the acidic catalyst and may, for example, be a tubular reactor. Aldehyde and alcohol have already reacted partly in the prereactor, so that a mixture of reactants and the acetal and also water in some cases leaves the prereactor and is fed to the reaction/distillation zone of the column. The conversion in the prereactor based on the reactant used in stoichiometric deficiency is 10-50%, preferably 15-40%.

The molar ratio of aldehyde and alcohol may vary within a relatively wide range around the stoichiometric equivalence of aldehyde:alcohol=0.5. When the possibility is available of using or working up one of the two reactants in an integrated process, it Is possible to virtually fully react the other reactant In each case by means of a stoichiometric excess of this reactant In preferred embodiments of the invention, the molar aldehyde:alcohol ratio is between 0.26 and 1.0. The overall conversion in the prereactor and reactive column in the process according to the invention is more than 80%, preferably more than 90% and more preferably more than 95%, based on the reactant used in stoichiometric deficiency.

For the preparation of methylal from formaldehyde and methanol, the reactive column is operated close to standard pressure, preferably at 20-250 mbar gauge. The bottom heating is adjusted such that a bottom temperature of 95-105° C. is established. The temperature in the reaction/distillation zone is 50-90° C. The temperature at the top of the column is 40-50° C.

The rectifying section of the column, arranged above the reaction/distillation zone, may, according to the prior art, be configured as a tray column, for example as a sieve tray column or bubble-cap tray column, or as a packed column with a structured or a random packing. An extractant is fed into the rectifying section of the column in order to enrich the alcohol in the ascending vapor mixture. A suitable feed distributor ensures that the extractant is distributed over the entire column cross section and good mass transfer with the ascending vapor occurs. The extractant is preferably a substance which is present In the process in any case, especially a substance which is readily miscible with the alcohol and less volatile than it. In the preferred preparation of methylal from methanol and formaldehyde, the extractant is an aqueous solution, for example a dilute formaldehyde solution. In a particularly preferred embodiment, the extractant is demineralized water.

The vapor stream leaving via the top of the column is condensed fully and fed partly back into the column above the rectifying section. The reflux ratio R of the column, where R is defined by the following ratio $R$=reflux/withdrawal, is adjusted depending on the requirements on the process. A high reflux ratio gives rise to a relatively high purity of the top product but results in a higher specific energy consumption. R in the process according to the invention is between 0.5 and 10, preferably between 1 and 8 and more preferably between 2 and 6.

The purity of the acetal at the top of the reactive column according to the invention is more than 90%. In the case of the preparation of methylal from formaldehyde and methanol, the top concentration is preferably more than 95% by weight of methylal and less than 2% by weight of methanol and less than 3% by weight of water. The top concentrations are more preferably more than 97% by weight of methylal with less than 1% by weight of methanol and less than 2% by weight of water. Very particular preference Is given to more than 98% by weight of methylal with less than 0.5% by weight of methanol and less than 1% by weight of water. According to the invention, the concentration of formaldehyde in the top product is less than 0.25% by weight, preferably less than 0.15% by weight and more preferably less than 0.10% by weight.

The top product thus obtained is purified to a purity of at least 99% in not more than two subsequent separation steps. This may, for example, be an extractive rectification to remove the water and a portion of the methanol. For high purity requirements, a distillation to remove low boilers may be added on. It is also possible first to remove the low boilers by distillation and then to add on an extractive rectification. Combinations with other basic operations such as extraction or drying are also possible.

In a preferred embodiment of the invention, methylal is freed of low boilers by distillation and of residual water and methanol by an extractive rectification, The extractant is involatile and water-miscible, for example a polyhydric alcohol having 2-4 carbon atoms, preferably ethylene glycol. The pure acetal product after the not more than two separation steps preferably has a purity of at least 99.9%.

Further preferred embodiments of the invention are evident from the subclaims.

EXAMPLE

The invention is illustrated with reference to a working example and to a FIGURE.

In a column of diameter 350 mm, sections 3, 4 and 6 are charged with Katapak elements (product from Sulzer Chemtech), whose pockets have been filled with an acidic ion exchange resin. Between sections 4 and 5, the effluent of a prereactor likewise filled with acidic ion exchange resin is fed in. 280 kg/h of a 20% aqueous formaldehyde solution are fed to the prereactor together with 100 kg/h of methanol. The prereactor is temperature-controlled to 80° C. Its effluent is composed of 19.5% methanol, 11.5% formaldehyde, 8% methylal and 61% water, corresponding to a conversion of 26% of the methanol in the prereactor. The column bottom is heated with approx. 120 kg/h of low-pressure steam, so that a temperature of 100° C. is set in the bottom, a temperature of 50° C. in the Katapak bed and a temperature of 46° C. at the top of the column.

Between section 5 and 6 of the reaction column, 100 kg/h of demineralized water are fed in via a distributor tray. The vapor of the column is condensed fully, 500 kg/h of the distillate are recycled to the top of the column as reflux and 110 kg/hour of crude methylal are withdrawn. The crude methylal has a composition of 98.2% methylal, 0.4% methanol, 0.8% water and 0.6% methyl formate. The bottom stream of the reactive column of 380 kg/h contains 1% methanol and 4% formaldehyde. The conversion based on methanol is 95.5%.

After a subsequent distillation of the low boilers and an extractive rectification with ethylene glycol, pure methylal of over 99.9% purity is obtained, which contains less than 100 ppm of methanol, less than 50 ppm of water and less than 100 ppm of methyl formate.

What is claimed is:

1. A process for preparing acetals from aldehydes and alcohols by reactive distillation, which comprises
   a) feeding aldehyde and alcohol to the reaction/distillation zone of a distillation column and at least partly converting them to the acetal,
   b) heating the column bottom disposed below the reaction/distillation zone,
   c) feeding an extractant into a rectifying section of the column, disposed above the reaction/distillation zone and
   d) condensing a product having more than 90% by weight of acetal at the top of the column and wherein the reactive distillation and the extractive distillation are combined in one column and wherein the reaction/distillation zone is obtained by charging one or more sections of the column with an acidic fixed bed catalyst.

2. The process as claimed in claim 1, wherein the reaction/distillation zone consists of one or more sections of the column which are charged with an acidic fixed bed catalyst.

3. The process as claimed in claim 1, wherein a reflux ratio between R=0.5 and R=10 is set in the column.

4. The process as claimed in claim 1, wherein the top product of the column is concentrated to a content of at least 99% by weight of acetal by not more than two subsequent separating operations.

5. The process as claimed in claim 1, wherein aldehyde and alcohols having one or two carbon atoms are used as reactants.

6. The process as claimed in claim 5 for the preparation of methylal from formaldehyde and methanol.

7. The process as claimed in claim 1, wherein the reactants are mixed and fed to a prereactor before they are introduced into the reaction/distillation zone of the column.

8. The process as claimed in claim 7, wherein the conversion in the prereactor based on the reactant used in stoichiometric deficiency is 10-50%.

9. The process as claimed in claim 1, wherein the conversion, based on the reactant used in stoichiometric deficiency, is more than 80%.

10. The process as claimed in claim 1, wherein the extractant is a substance which is present in the process in any case.

11. The process as claimed in claim 1, wherein the extractant is water.

12. The process as claimed in claim 3, wherein the reflux ratio R is between 1 and 8.

13. The process as claimed in claim 1, wherein the top concentration is more than 95% acetal.

14. The process as claimed in claim 1, wherein the top concentration is more than 97% acetal.

15. The process as claimed in claim 1, wherein the top concentration is more than 98% acetal.

16. The process as claimed in claim 4, wherein the purity of the acetal after the subsequent not more than two separation steps is at least 99.9%.

17. The process as claimed in claim 7, wherein the conversion in the prereactor based on the reactant used in stoichiometric deficiency is 15-40%.

18. The process as claimed in claim 1, wherein the conversion, based on the reactant used in stoichiometric deficiency is more than 95% and the extractant is demineralized water and the reflux ratio R is between 2 and 6.

19. The process as claimed in claim 1, wherein the extractant is demineralized water.

20. The process as claimed in claim 1, wherein the reactive distillation zone consists essentially of 18 to 40% by weight of a formaldehyde solution, alcohol and an acidic fixed bed catalyst.

21. The process as claimed in claim 1, wherein said process is carried out in the absence of a defoamer.

* * * * *